United States Patent [19]

Insley et al.

[11] Patent Number: 4,964,509
[45] Date of Patent: Oct. 23, 1990

[54] UNIVERSAL SHIPPING CONTAINER FOR HAZARDOUS LIQUIDS

[75] Inventors: Thomas I. Insley, Lake Elmo, Minn.; James F. Dyrud, New Richmond, Wis.; Donald E. Young, Forest Lake, Minn.

[73] Assignee: Minnesota Mining and Manufacturing Co., Saint Paul, Minn.

[21] Appl. No.: 477,742

[22] Filed: Feb. 9, 1990

[51] Int. Cl.⁵ .................. B65D 81/26; B65D 81/02
[52] U.S. Cl. .................... 206/204; 206/523; 206/592; 206/433
[58] Field of Search ............... 206/204, 521, 523, 524, 206/591, 592, 433

[56] References Cited

U.S. PATENT DOCUMENTS

| | | | |
|---|---|---|---|
| 2,282,908 | 5/1942 | Thompson | 206/523 |
| 3,096,879 | 7/1963 | Schumacher | 206/523 |
| 3,146,929 | 9/1964 | Keim | 206/433 X |
| 3,181,693 | 5/1965 | Freistat | 206/523 |
| 3,311,231 | 3/1967 | English, Jr. | 206/523 |
| 3,871,521 | 3/1975 | Szatkowski | 206/524 |
| 4,129,213 | 12/1978 | Fleig | 206/523 X |
| 4,173,286 | 11/1979 | Stanko | 206/433 |
| 4,267,927 | 5/1981 | English, Jr. | 206/524 |
| 4,884,684 | 12/1989 | Bernardin et al. | 206/523 X |

*Primary Examiner*—William I. Price
*Attorney, Agent, or Firm*—Donald M. Sell; Walter N. Kirn; David W. Anderson

[57] ABSTRACT

A shipping or secondary container, which can safely transport a plurality of breakable primary containers of a variety of sizes and shapes, has a pair of rigid shells that mate. A batt of sorptive material fills each shell, and a normally tacky, discontinuous adhesive layer covers the exposed face of at least one batt. The shells can be vacuum formed from a sheet of thermoplastic resin that is 0.25 to 0.5 mm in thickness. The two shells preferably are identical to each other. To permit them to interlock, each shell has an upstanding wall that is formed with both tongues and grooves which telescopically mate with the tongues and grooves of the other shell.

18 Claims, 2 Drawing Sheets

UNIVERSAL SHIPPING CONTAINER FOR HAZARDOUS LIQUIDS

BACKGROUND OF THE INVENTION

1. Field of the Invention

The invention concerns packages for transporting breakable vials of liquids that are possibly hazardous, e.g., diagnostic specimens, etiologic specimens, and fine chemicals. More specifically, the invention is concerned with containing liquids accidentally released from a vial through breakage or leaking as well as preventing the liquid from contaminating other vials in the package, thus safeguarding persons who handle the package or the vials.

In the art, a breakable vial is generally called a "primary container," and a package for a plurality of primary containers is generally called a "secondary container." Below, a secondary container is sometimes called a "shipping container."

2. Description of the Related Art

Currently, a significant portion of medical specimens are transported from laboratories and medical centers to large diagnostic centers for analyses. The diagnostic specimens (e.g., blood) typically are transported in breakable primary containers such as test tubes, syringes, and vials which in turn are packaged in secondary or shipping containers that cushion the primary containers against shock. Even so, leakage or breakage frequently occurs, and because of the possibly hazardous nature of the liquids, the secondary containers should be designed to contain the liquids so that the liquid cannot contaminate other primary containers in the package or be released to the environment.

Diagnostic specimens typically are transported in a secondary container, e.g., molded styrofoam, that has a pocket for each primary container. For example, see a 3-tube, blood sample mailer (stock No. 193–508) from Curtin Matheson Scientific Inc. When a primary container is significantly smaller than its pocket, it may be wrapped in tissue or toweling to make it fit more snugly, and the packing material may be able to absorb or adsorb liquid released by a broken or leaking primary container. However, any sorbent protection that such a sheet may afford is haphazard and gives no assurance against injury to handlers.

Even when a shipping container arrives at a diagnostic center without damage, there is a need to minimize the hazard that upon being opened, a primary container might fall out of the shipping container and break. A certain amount of carelessness can be expected whenever persons are handling large numbers of containers on a routine, daily basis.

When the layout for the primary containers within any such secondary container is specifically designed or configured for one laboratory, the utility of the secondary container may be significantly diminished for other laboratories that employ primary containers of different types, shapes, sizes or numbers. Accordingly, it can be expensive and difficult for vendors to supply customized containers for the special needs of every laboratory or group of laboratories. For one special design, see the secondary container of U.S. Pat. No. 4,240,547 (Taylor) that has tubular cavities for a number of test tubes plus a rectangular slide holder aperture. The Taylor secondary container is formed with a central recess through which leaking liquid should flow and an absorbent material filling that recess, the purpose of which is to absorb liquid before it can leak outside the secondary container. Another special multi-pocket design is shown in U.S. Pat. No. 3,621,994 (Brown).

When a breakable primary container contains a hazardous liquid, it typically is packaged by itself in a secondary container that may include sorptive material to prevent any liquid from accidentally leaking out of the container. See U.S. Pat. Nos. 3,999,653 (Haigh et al.); 4,560,069 (Simon); 4,573,578 (Greminger et al.); and 4,756,937 (Mentzer). While the secondary container of the Mentzer patent has only one pouch, the Mentzer patent says that more than one primary container can be transported in that pouch. The material of which the Mentzer secondary container is made entraps "an antidote" with which leaking liquid can react to produce a gel.

Other secondary containers that are formed with individual pockets for primary containers are U.S. Pat. Nos. 3,146,929 (Keim) for jars of baby food; 3,871,521 (Szatkowski); and 4,173,286 (Stanko) for beverage cans.

SUMMARY OF THE INVENTION

The invention provides a shipping or secondary container which is believed to be the first that can safely transport a plurality of breakable, liquid-filled primary containers of a variety of sizes and shapes and also ensures against the escape of leaking liquid from the shipping container. Briefly, the shipping container of the invention comprises a pair of rigid shells that mate to enclose a space, a batt of sorbent material filling each shell, which batt has a normally substantially flat exposed face, is sufficiently conformable to envelop a primary container when the shells are closed, and has sufficient body to keep the primary container at the interface between the batts when the shells are closed, and a normally tacky, discontinuous adhesive layer on the exposed face of at least one batt.

Batts based on materials similar to those described in U.S. Pat. No. 4,813,948 (Insley), when used in the novel shipping container of the present invention, can completely surround and isolate each of a plurality of cylindrical primary containers that is spaced from any adjacent container by at least the sum of the radii of the two containers. Even when batts of the novel secondary container have inferior sorbency such as an open-cell foam, the leakage should be prevented from escaping from the novel secondary container when the shells have been vacuum formed of thermoplastic resin and their juncture is sealed by a liquid-impervious adhesive tape. To protect the surface of the batt, it can have a scrim facing or covering such as spun-bond polypropylene fabric.

A normally tacky, discontinuous adhesive layer can be applied to the faces of the batts by hot-melt spraying. At low application levels, such spraying inherently produces a discontinuous adhesive layer that can have a stringy appearance. Instead of being sprayed, the adhesive layer may also be applied by pattern coating or by print coating to produce a discontinuous adhesive layer. Because it is discontinuous, the adhesive layer does not interfere with the passage of liquid from a broken or leaking primary container into the batts.

By applying adhesive to both faces of a batt, one layer of adhesive bonds the batt its shell and the other adhesive layer holds primary containers in place during shipment and after the novel secondary container has been opened. Preferably only one exposed face of the two batts bears an adhesive layer so that all of the primary containers remain on the same batt. After the novel secondary container has been opened, leaving primary containers on one shell, at least half of each primary container is fully exposed and easy to grasp securely, thus minimizing any danger of dropping it. In contrast, the pockets of prior secondary containers can inhibit the removal of a primary container and thus create a danger of it being dropped.

Preferred pressure-sensitive adhesives are so-called "low-tack" rubber-resin compositions that nevertheless have sufficient adhesion to glass or plastics typically used as primary containers that the discontinuous adhesive layer holds a liquid-filled primary container in position, regardless of the magnitude or frequency of shocks encountered in shipment. Such an adhesive also holds the liquid-filled primary container in place after the container has been opened, even when the shell is tipped. Experiments indicate that until the primary containers are lifted from the batt, a tacky adhesive that permits easy removability will hold a liquid-filled primary container in place when the shell is tipped until the exposed face of the batt is almost vertical. Such tackiness makes it very unlikely that a primary container will accidentally fall off. On the other hand, an overly tacky adhesive could make it difficult to separate the primary container from the container.

For economy and to keep it light in weight, the shells of the secondary container preferably are vacuum formed from a sheet of thermoplastic resin that is from about 0.25 to 0.5 mm in thickness. Preferred thermoplastic resins of which the shells may be molded include plasticized polyester resins and plasticized poly(vinylchloride), each of which retains good toughness at temperatures as low as −30° C. and is inexpensive. To permit the novel secondary container to hold a plurality of primary containers, each shell preferably has a broad face extending parallel to the exposed face of its batt and upstanding walls that are short relative to the length and breadth of the broad faces. To enhance rigidity, the broad face of each shell preferably is ribbed. When the broad faces of the two shells are substantially flat and parallel to each other, each batt is of uniform thickness and accordingly is equally compressible over its entire face.

For economy of manufacture and inventory, the two shells preferably are identical to each other. To permit them to interlock, each upstanding wall is formed with both tongues and grooves which telescopically mate with the tongues and grooves of the other wall. Such mating reinforces the novel secondary container and also slightly compress the batts, thus enabling the batts to lend a reinforcing effect. Additional reinforcement is provided when the novel secondary container is holding a plurality of primary containers which further densify and stiffen the batts. Hence, the novel secondary container is capable of withstanding shocks commonly encountered in shipping, even when the shells have a thin, lightweight construction.

After primary containers have been laid onto said adhesive layer and the other shell has been positioned to close the shipping or secondary container, the juncture between the shells preferably is completely sealed with an adhesive tape that preferably has a nonporous backing. In the unlikely event that liquid released from a primary container would seep through the batts to reach the margins of the shell, the nonporous backing of the adhesive sealing tape should act as a barrier to prevent the passage of the liquid beyond the confines of the secondary container. Preferably the adhesive of the sealing tape is a pressure-sensitive adhesive, thus making it easier to apply the tape to the secondary container and to subsequently open it.

The batts preferably readily sorb both aqueous and oil-based liquids. When loaded to 50% of their saturation capacity, the batts should retain a sorbed liquid when subjected to a force that compresses the batt to about 50% of its original thickness. Such a batt can be made as described in U.S. Pat. No. 4,813,948 (Insley) wherein microwebs made by tearing apart source webs of blown microfibers which have been sprayed with a nonionic surfactant have been incorporated into a blown microfiber carrier web. The microfibers of both the microwebs and carrier web preferably have an average fiber diameter of than about 10 $\mu$m and have both good conformability and good body coupled with excellent sorbency of liquids. As taught in the Insley patent, the blown microfibers may also be loaded with particulate material. The particulate material can be selected to neutralize potentially hazardous liquids to be transported in primary containers. For example, see U.S. Pat. No. 3,971,373 (Braun).

THE DRAWING

The invention may be more easily understood in reference to the drawing, all figures of which are schematic. In the drawing.

Figure 1:
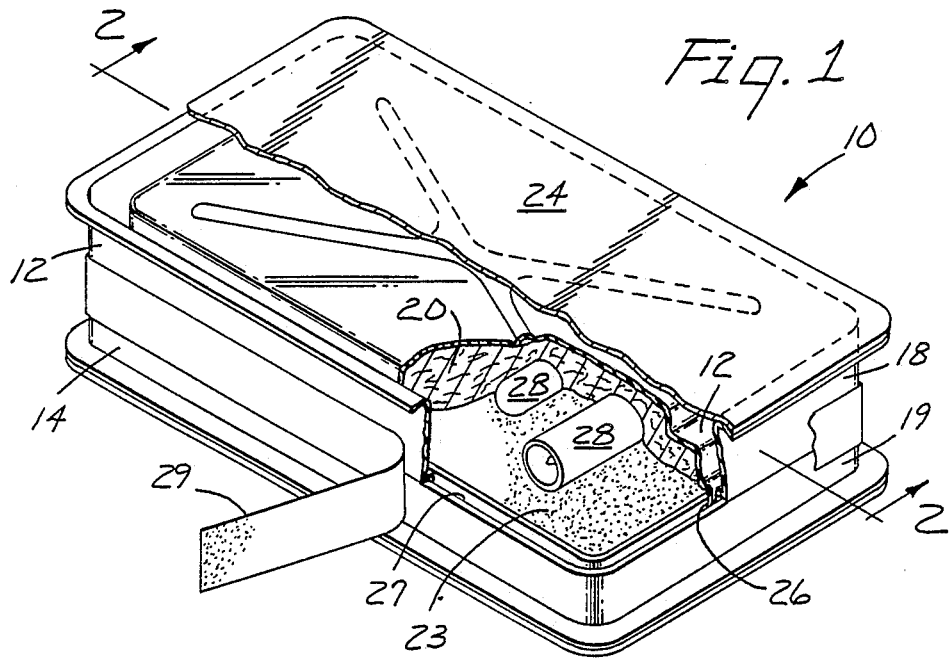
FIG. 1 is a perspective view of a preferred shipping container of the invention, partly broken away to show details.
Figure 2:
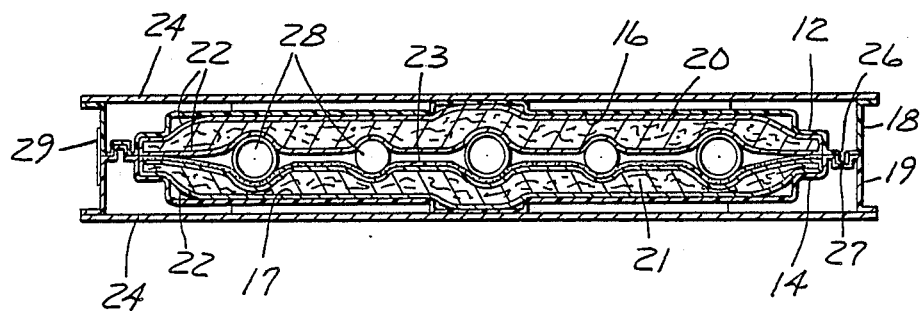
FIG. 2 is cross section of the container of FIG. 1 taken at line 2—2 of FIG. 1.

The shipping container 10 of FIGS. 1 and 2 has two identical shells 12 and 14 having a substantially rectangular broad ribbed faces 16 and 17 and short upstanding wall 18 and 19, respectively. Filling the shells 12 and 14 are batts 20 and 21, respectively. Extending across each broad face of each batt is a scrim 22. A discontinuous layer of adhesive 23 (not shown in FIG. 2) covers the face of the scrims that contact a ribbed face of a shell. The exposed surface of the scrim on one batt 21 also bears a discontinuous adhesive layer 23. Adhesively bonded to a flange of each shell 12 and 14 is a paperboard sheet 24. A tongue 26 extends halfway around the perimeter of the upstanding wall 18 and telescopically mates with a groove 27 that extends halfway around the perimeter of the upstanding wall 19.

When a plurality of spaced-apart, liquid filled primary containers 28 are placed on the discontinuous adhesive layer 23 and the shipping container 10 is closed as shown in FIG. 2, the batts 20 and 21 completely surround and isolate each primary container 28. A pressure-sensitive tape 29 seals the junction between the two shells.

Test Procedures

Demand Sorbency

A 4.45 cm (1.75 in.) diameter test sample of microweb sorbent material was placed on a 25–50 $\mu$m porous plate in a filter funnel. A pressure of 1.0 kPa is applied to the sample by a plunger which is freely movable in the barrel of the funnel. Deionized water at zero hydrostatic head is conducted from a reservoir through a siphon mechanism to the upper surface of the porous plate where the test sample sorbed the water. The "Demand Sorbency," which is the initial lineal rate of absorbency is determined and reported in $1/m^2/min$.

Centrifugal Retention

A sample of microweb sorbent material, saturated to equilibrium saturation with deionized water in the demand sorbency test funnel, is placed in a centrifuge tube which is placed in a centrifuge and subjected to a centrifugal force of 180 G for 10 minutes. The sample is removed and the amount of deionized water remaining in the sample is determined by weight differential and is reported as "Centrifugal Retention" in g/g.

Sorbency

A sample of the microweb sorbent material (21.6 cm×27.9 cm) is placed in a tray containing deionized water to a depth of at least 25 cm. The sample is allowed to rest on the surface of the water for one minute, and if not saturated, is submerged in the water for two minutes, after which it is removed from the water, placed on a drain screen and allowed to drain for two minutes. The amount of water remaining in the sample is determined by weight differential. The "Sorbency" is the amount of deionized water remaining in the sample per sample weight (g/g).

Thickness

The "Thickness" of microweb sorbent material was determined using a low-load caliper tester Model No. CS-49-051, available from Custom Scientific Instruments, Inc., with a 1.22 g balance weight.

Compressive Stress/Strain Test

Specimens of 15 cm×15 cm are subjected to compressive stress using a Instron test unit incorporating a compression load cell and a 5 cm diameter compression foot. The deflection of the specimen over a range of loading is recorded using a uniform loading rate. Evaluations were conducted using a X-head speed of 1.0 cm/min. The force applied to the sample (stress) is recorded in KPa where the deflection (strain) is reported as a percentage of the uncompressed thickness.

Drop Test

Four stoppered glass test tubes, 1.5 cm in diameter by 9.5 cm long and filled with colored water, are placed in parallel rows in a shipping container, the test tubes being spaced 5 cm from adjacent test tubes and the ends of the package. The package is sealed with tape and subjected to a drop test at room temperature as outlined in the United Nations Transport of Dangerous Goods Section 9.7.3a, Package Group 1. Criteria for passing the test, which included dropping the package five times from a height of 1.8 m, once flat on the bottom, once flat on the top, once flat on a long side, once flat on a short side and once on a corner, requires that the outer package should not "exhibit any damage liable to affect safety during transport" and that there be no leakage from the inner receptacle or inner packaging.

Penetration Test

Four stoppered glass test tubes, 1.5 cm in diameter by 9.5 cm long and filled with colored water, are placed in parallel rows in a completed shipper package, the test tubes being spaced 5 cm from adjacent test tubes and the ends of the package. After being sealed with tape, the shipping container is subjected to a impact/penetration test as described in Title 49 of the Code of Federal Regulations Section 173.387, paragraph (b)(2)(iii). The test involves dropping a steel bar of specified nose radius onto the package and then monitoring the package for potential release of its contents to the environment. A worst case scenario is simulated by dropping the bar on the container directly above one of the test tubes. A piece of white absorbent paper is placed under the shipping container prior to the bar drop to help visualize leakage. In order to pass this test, a shipping container must not release any colored water to the environment, and the continuing effectiveness of the shipping container must not be significantly reduced.

EXAMPLE 1

Microweb Microfiber Source Web

A blown microfiber (BMF) source web was prepared according to U.S. Pat. No. 4,933,229, (T. I. Insley and D. E. Meyer), which is incorporated herein by reference, that had an average fiber diameter of 6–8 μm, a basis weight of 300 gm/m² and contained 8% by weight "Triton" X-100, a poly(ethylene oxide) based nonionic surfactant available from Rhom and Haas Corp.

Shell of Shipping Container

Each of the two identical shells as illustrated in FIGS. 1 and 2 was prepared by vacuum forming a 0.38 mm thick sheet of Kodar PETG6763, a thermoplastic glycol modified polyethylene terephthalate resin, available from Eastman Chemicals, at 121–163° C. over a male mold to produce a rectangular shell (25 cm×14 cm×4 cm). Each shell had a face thickness of 0.33 mm, a side wall thickness of 0.16 mm and a corner thickness of 0.30 mm. A paperboard backing (0.38 mm thick) was adhesively secured to the flange of each shell.

The Batts

The previously described microweb microfiber source web was divellicated into microwebs and incorporated into a BMF carrier web according to U.S. Pat. No. 4,813,948 (Insley), which is incorporated herein by reference. The carrier web, which contained 8 percent by weight "Triton" X-100, was prepared according to previously cited U.S. Pat. No. 4,933,229, (T. I. Insley and D. E. Meyer) and microwebs were incorporated into the carrier web at a 50 wt. % level to produce a microweb sorbent material having a basis weight of 400 g/m², a density of $2.6 \times 10^{-2}$ g/cm³, a solidity of 2.8%, and a thickness of 2.0 cm. The microweb sorbent material showed a Demand Sorbency of 4.95 $1/m^2/min$, a Centrifugal Retention of 0.4 g/g, and a Bulk Sorbency of 22.8 g/g. The shock protection properties of the sorbent material were characterized by the previously described Stress/Strain test, the results of which are graphically presented in FIG. 3 and discussed below.

A pair of sorbent batts were prepared by applying a rubber/resin based hot-melt pressure-sensitive adhesive (PSA) designation No. 34-5511, available from National Starch Corp., to both faces of an approximately 14 cm×55 cm scrim material (51 g/m² "Celestra," a spunbond polypropylene nonwoven web available from James River Corp.) and adhering the scrim to the microweb sorbent material (approximately 14 cm×25 cm×2 cm, 14.0 g in weight) by wrapping the PSA coated scrim lengthwise around the sorbent material and overlapping the ends of the scrim. Each of the batts was placed in one of the shells to provide the shipping container of Example 1.

The shipping container was loaded with stoppered, liquid-filled test tubes as dictated by the above described Drop test, and the juncture between its shells was sealed with 3M Brand #396 PSA tape (2.54 cm width). The sealed shipping container passed the previously described Drop Test, i.e., no significant damage to the shipper container, no shifting of the test tubes within the shipper and no leakage of the test tube contents.

EXAMPLE 2

A shipping container was made in as in Example 1 except that the microweb sorbent material incorporated poly(ethylene phthalate) staple fiber (15 denier, 3.2 cm in length, Type Kodel 431, available from Eastman Chemical) in addition to the microwebs. The composition of the microweb sorbent material was 50 wt. % carrier web, 30 wt. % microwebs and 20 wt. % staple fibers. The microweb sorbent material had a basis weight of 415 g/m$^2$, a density of $2.1 \times 10^{-2}$ g/cm$^3$, a solidity of 2.1% a thickness of 2 cm, a Demand Sorbency of 4.95 1/m$^2$/min, a Centrifugal Retention of 0.35 g/g, and a Bulk Sorbency of 26 g/g.

When subjected to the previously described Penetration Test, one plastic shell of the shipping container was crushed, but not punctured, and crazing of the plastic shell was noted. The tape seal remained intact, thereby maintaining the integrity of the shipping container of Example 2. The test tube immediately below the point of impact of the test bar broke, releasing its contents into the sorbent batt with minimal spreading (i.e., the colored water did not contact adjacent test tubes and no fluid escaped from the shipping container).

For comparison, a styrofoam specimen case utilized commercially by International Chemical Laboratories (ICL) was also subjected to the Penetration test. It split essentially in half along the width of the case, and a significant amount of colored water leaked out of the case.

Figure 3:
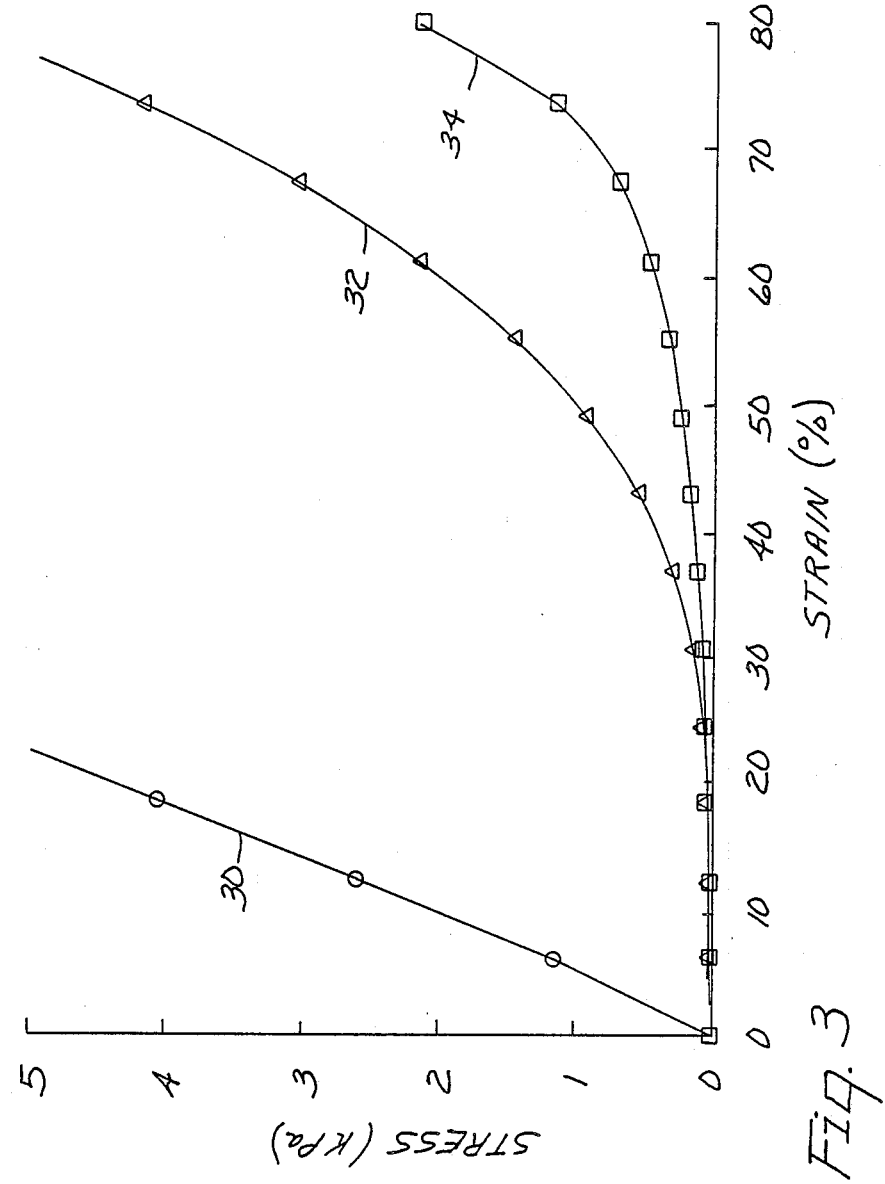
FIG. 3 is a graph showing compressive stress/strain characteristics of three batts which can be employed in the shipping containers of the invention.

Compressive Stress/Strain Curves of FIG. 3

Three sorbent materials that can be used to make the batts for the novel shipping containers were subjected to the previously described Compressive Stress/Strain Test. In FIG. 3, curve 30 was obtained using an open-cell foam having a density of $1.7 \times 10^{-2}$ g/cm$^3$ that is currently being used in shippers for diagnostic specimens. Curve 32 was obtained using a commercially available sorbent material (3M Brand "Powersorb" universal sorbent which is a hydrophilic microfiber material). Curve 34 was obtained using the microweb sorbent material of Example 2.

A continuation of curve 30 (not illustrated) is substantially a straight line up to at least the 80% compression level. Materials having curves like curve 30 would provide good cushioning characteristics but would require high compressive forces to conform to a primary container when used in a batt of the novel shipping container. Because of this limited conformability and its poor sorbency, the foam would not be preferred for use in the invention.

Preferred sorbent materials include those having compressive stress/strain curves similar to curves 32 and 34. Their initial relatively shallow slopes are indicative of good conformability, and their shapely steepening slopes above about 50% and 70% strain respectively, are indicative of good cushioning properties. For fragile, light weight primary containers such as glass test tubes, sorbent materials having compressive stress/strain curves like curve 34 are preferred. For more durable and heavier primary containers, sorbent materials having compressive stress/strain curves similar to curve 32 are preferred.

We claim:

1. Universal shipping or secondary container suitable for transporting a plurality of breakable, liquid filled primary containers of various sizes and shapes, which shipping container comprises
    a pair of rigid shells that mate to enclose a space,
    a batt of sorbent material filling each shell, which batt
        has a normally substantially flat exposed surface,
        is sufficiently conformable to envelop a primary container when the shells are closed, and
        has sufficient body to keep the primary container at the interface between the batts when the shells are closed, and
    a normally tacky, discontinuous adhesive layer on the exposed surface of the batt of at least one of the shells.

2. Shipping container as defined in claim 1 wherein each of said shells comprises a thermoplastic resin that retains good toughness at temperatures as low as $-30°$ C.

3. Shipping container as defined in claim 2 wherein said shells have been vacuum formed and the thermoplastic resin comprises a plasticized vinyl resin.

4. Shipping container as defined in claim 3 wherein the plasticized vinyl resin comprises poly(vinyl chloride).

5. Shipping container as defined in claim 1 each batt comprises blown microfibers that have an average fiber diameter of less than about 10 μm.

6. Shipping container as defined in claim 5 wherein the blown microfiber batt is sandwiched between two scrims.

7. Shipping container as defined in claim 6 wherein said scrims comprise spun-bonded polypropylene.

8. Shipping container as defined in claim 5 wherein the batts are sufficiently conformable to surround and isolate two adjacent cylindrical primary containers that are spaced by at least the sum of their radii.

9. Shipping container as defined in claim 1 wherein each of said shells has a broad, substantially flat face which is parallel to the exposed face of its batt.

10. Shipping container as defined in claim 9 wherein the broad face of each shell is ribbed.

11. Shipping container as defined in claim 1 wherein the two shells are identical to each other.

12. Shipping container as defined in claim 10 wherein each shell has an upstanding wall that is formed with both tongues and grooves which telescopically mate with the tongues and grooves of the other shell.

13. Shipping container as defined in claim 1 wherein the juncture between the mating shells is completely sealed with an adhesive tape.

14. Shipping container as defined in claim 1 wherein said adhesive tape has a nonporous backing.

15. Shipping container as defined in claim 14 wherein said adhesive of said adhesive tape is a pressure-sensitive adhesive.

16. Shipping container as defined in claim 1 wherein said discontinuous adhesive layer is stringy.

17. Shipping container as defined in claim 1 wherein said discontinuous adhesive is a rubber-resin composition.

18. Shipping container as defined in claim 17 wherein said discontinuous adhesive has sufficient adhesion to hold a liquid-filled glass primary container in position on the exposed face of a batt after the shipping container has been opened and the shell has been tipped until the exposed face of the batt is almost vertical.

* * * * *